US00RE39078E

(19) United States
(12) Reissued Patent
Dedieu et al.

(10) Patent Number: US RE39,078 E
(45) Date of Reissued Patent: Apr. 25, 2006

(54) RECOMBINANT ADENOVIRUSES FOR GENE THERAPY IN CANCERS

(75) Inventors: Jean-Francois Dedieu, L'Hay les Roses (FR); Aude Le Roux, Thiais (FR); Michel Perricaudet, Ecrosnes (FR)

(73) Assignee: Gencell SA, Vitry-sur-Seine (FR)

(21) Appl. No.: 09/654,223

(22) PCT Filed: Nov. 7, 1994

(86) PCT No.: PCT/FR94/01284

§ 371 (c)(1),
(2), (4) Date: May 13, 1996

(87) PCT Pub. No.: WO95/14101

PCT Pub. Date: May 26, 1995

Related U.S. Patent Documents

Reissue of:
(64) Patent No.: 5,837,531
Issued: Nov. 17, 1998
Appl. No.: 08/646,246
Filed: May 13, 1996

(30) Foreign Application Priority Data

Nov. 18, 1993 (FR) ..... 93 13766

(51) Int. Cl.
*A61K 48/00* (2006.01)

(52) U.S. Cl. ..... 424/93.2; 435/69.1; 435/320.1; 435/91.4

(58) Field of Classification Search ..... 424/93.2; 435/69.1, 320.1, 91.4, 325; 514/44
See application file for complete search history.

(56) References Cited

U.S. PATENT DOCUMENTS

| | | | | | |
|---|---|---|---|---|---|
| 4,939,088 | A | * | 7/1990 | Young et al. | 435/320.1 |
| 5,194,601 | A | * | 3/1993 | Sugden et al. | 435/320.1 |
| 5,631,236 | A | * | 5/1997 | Woo et al. | |
| 5,672,344 | A | | 9/1997 | Kelley et al. | 424/172.1 |

FOREIGN PATENT DOCUMENTS

| | | | |
|---|---|---|---|
| WO | WO 92/05262 | * | 4/1992 |
| WO | WO 93/19191 | * | 3/1993 |
| WO | WO 93/19191 | | 9/1993 |

OTHER PUBLICATIONS

Stefan Karlsson (1991) Blood, vol. 78, No. 10: pp. 2481–2492.*
Dong et al. (1996) Human Gene Therapy 7: 319–331.*
Morsy et al. (Nov. 17, 1993) JAMA, vol. 270, No. 19, pp. 2338–2345.*
Ronald Crystal (1995) Science, vol. 270, pp. 404–409.*
Coghlan (25 Nov., 1995) New Scientist pp. 14–15, vol. 149.*
Marshall (Aug. 1995) Science, vol. 269, pp. 1050–1055.*
Marshall (Dec. 1995) Science, vol. 270, p. 1751.*
Orkin & Moltulsky (Dec. 7, 1995) NIH Report on Gene Therapy.*
Sugden et al. (1989) Journal of Virology, pp. 2644–2649.*
Zimber–Strobl et al. (1991) Journal of Virology, pp. 415–423.*
Perricaudet et al. (1992) Ann Oncol., vol. 3, suppl. 5, p. 135.*
Mastrangelo et al (1993) The Journal of Clinical Investigation, vol. 91, pp. 225–234.*
Jean Marx (1993) Science, vol. 259, pp. 760–761, Jul. 30, 1996.*
Kozarsky et al. (1993) Current Opinion in Genetics and Development, 3, pp. 499–503, Jul. 30, 1996.*
Haddada et al. Defective recombinant adenoviruses expressing cytokines for use in antitumoral treatment pp. 1–22 1995.*
Phelps et al. Analysis or trans activation by human papillomavirus type 16 E7 and adenovirus 12S E1A suggests a common mechanism vol. 65 No. 12 1991 pp. 6922–6930.*
EBNA2 can activate transcription via E2 factor binding sites pp. 165–168 1993 vol. 225.*
Clayman et al., "*Adeno p53 Gene Transfer in a Phase I/II Trial of Patients with Advanced Recurrent Head and Neck Squamous Carcinoma*," Soc. for Biol. Therapy, Ann. Meeting, Abstract (1996).
Clayman et al., "*Adenovirus Mediated p53 Gene Transfer in a Phase I Trial of Patients with Advanced Recurrent Head and Neck Squamous Carcinoma*," ASCO Annual Meeting, Abstract (1997).
Clayman et al., "*Adenovirus Mediated p53 Gene Transfer in Patient with Advanced Recurrent Head and Neck Squamous Carcinoma*," AACR Annual Meeting, Abstract.
Clayman et al., "*Gene Therapy for Head and Neck Cancer: Comparing the Tumor Suppressor Gene p53 and a Cell Cycle Regulator WAFI/CIP1* (p 21)," Arch. Otolaryngol. Head Neck Surgery, vol. 122, pp. 489–493 (1996).
Coghlan, "*New Scientist*," vol. 149, pp. 14–15 (1995).
Crystal, "*Transfer of genes to humans: early lessons and obstacles to success*," Science vol. 270, pp. 404–409 (1995).
Dong et al., "*Systematic analysis of repeated gene delivery into animal lungs with a recombinant adenovirus*," Human Gene Therapy vol. 7, pp. 319–331 (1996).
Karlsson, "*Treatment of genetic defects in hematopoietic cell function by gene transfer*," Blood, vol. 78, No. 10, pp. 2481–2492 (1991).
Kozarsky et al., "*Gene therapy: adenovirus vectors*," Current Opinion on Genetics and Development, vol. 3, pp. 499–503 (1996).
Marshall, "*Gene therapy's growing pains*," Science, vol. 269, pp. 1050–1055 (1995).

(Continued)

*Primary Examiner*—Dave T. Nguyen
(74) *Attorney, Agent, or Firm*—Finnegan, Henderson, Farabow, Garrett & Dunner, L.L.P.

(57) ABSTRACT

The invention concerns recombinant viruses comprising a heterologous DNA sequence under the control of expression signals specifically active in tumor cells, and their preparation and use in the treatment and prevention of cancers.

24 Claims, 1 Drawing Sheet

OTHER PUBLICATIONS

Figure 1:
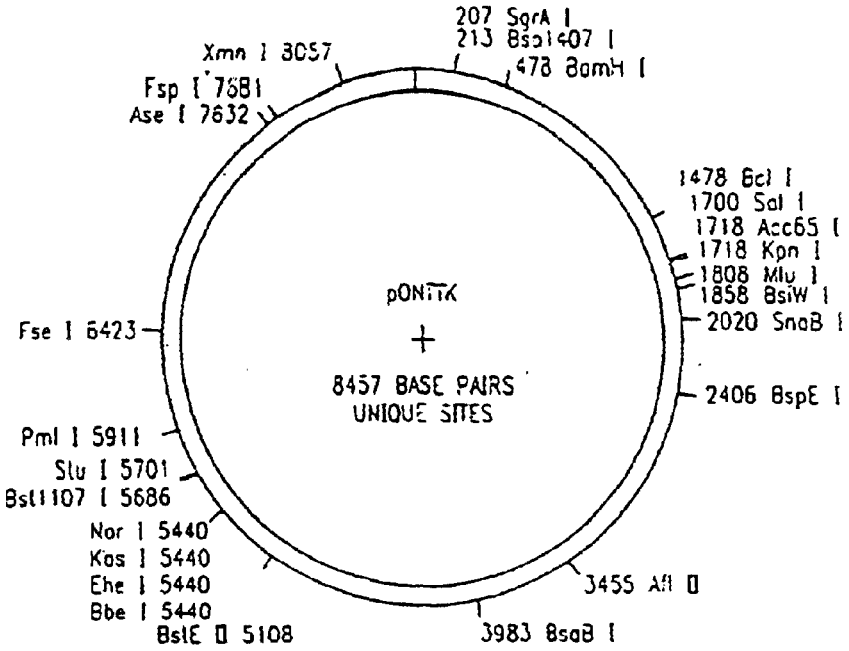

Marshall, "*Less hype, more biology needed for gene therapy*," Science, vol. 270, p. 1751 (1995).
Marx, "*Cell death studies yield cancer clues*," Science, vol. 259, pp. 760–761 (1996).
Mastrangeli et al., "*Diversity of airway epithelial cell targets for in vivo recombinant adenovirus–mediated gene transfer*," The Journal of Clinical Investigation, vol. 91, pp. 225–234 (1993).
Morsy et al., "*Progress toward human gene therapy*," JAMA, vol. 270, No. 19, pp. 2338–2345 (1993).
Orkin & Moltulsky, NIH Report on Gene Therapy, (Dec. 7, 1995).
Roth et al., "*Retrovirus–Mediated Wild–Type p53 Gene Transfer to Tumors of Patients with Lung Cancer*," Nature Medicine, vol. 2, pp. 985–991 (1996).
Sugden et al., "*A promoter of Epstein–Barr virus that can function during latent infection can be transactivated by EBNA–1, a viral protein required for viral DNA replication during latent infection*," Journal of Virology, pp. 2644–2649 (1989).
Swisher et al., "*Persistant Transgene Expression Following Repeated Injections of a Recombinant Adenovirus Containing the p53 Wild–Type Gene in Patients with Non–Small Cell Lung Cancer*," AACR Annual Meeting, Abstract.
Swisher et al., "*Adenoviral Mediated p53 Gene Transfer in Patients with Advanced Non–Small Cell Lung Cancer (NSCLC)*," ASCO Annual Meeting, Abstract (1997).
Zimber–Strobl et al., "*Epstein–Barr virus nuclear antigen 2 activates transcription of the terminal protein gene*," Journal of Virology pp. 415–423 (1991).

* cited by examiner

RECOMBINANT ADENOVIRUSES FOR GENE THERAPY IN CANCERS

Matter enclosed in heavy brackets [ ] appears in the original patent but forms no part of this reissue specification; matter printed in italics indicates the additions made by reissue.

This application *is a reissue application of U.S. Pat. No. 5,837,531, which issued on Nov. 17, 1998, from U.S. application Ser. No. 08/646,246, which* is a national phase application under 35 U.S.C. 371 of PCT/FR 94/01284, filed Nov. 7, 1994*, which claims priority to FR 93 13766 filed Nov. 18, 1993*.

The present invention relates to recombinant vectors of viral origin and to their use for the treatment of cancers. More particularly, it relates to recombinant adenoviruses containing a heterologous DNA sequence under the control of expression signals which are active specifically in tumour cells. The invention also relates to the preparation of these vectors, to the pharmaceutical compositions containing them and to their use in gene therapy.

Gene therapy consists in correcting a deficiency or an abnormality (mutation, aberrant expression and the like) by the introduction of a genetic information into the cell or the affected organ. This genetic information can be introduced either in vitro into a cell extracted from the organ, the modified cell then being reintroduced into the body, or directly in vivo into the appropriate tissue. Various techniques have been described for the introduction of this genetic information, amongst which are various transfection techniques involving complexes of DNA and DEAE-dextran (Pagano et al., J. Virol. 1 (1967) 891), of DNA and nuclear proteins (Kanada et al., Science 243 (1989) 375), of DNA and lipids (Felgner et al., PNAS 84 (1987) 7413), the use of liposomes (Fraley et al., J. Biol. Chem. 255 (1980) 10431), and the like. More recently, the use of viruses as vectors for the transfer of genes appeared as a promising alternative to these physical transfection techniques. In this respect, various viruses have been tested for their capacity to infect certain cell populations, in particular retroviruses (RSV HMS, MMS and the like), HSV virus, adeno-associated viruses, and adenoviruses.

Numerous applications of gene therapy are under study, such as genetic diseases (myopathy, cystic fibrosis, SCID, and the like), pathologies of the central nervous system (Alzheimer, Parkinson, and the like), cardiovascular diseases (haemophilia, atherosclerosis), AIDS or cancers. More particularly, as regards the treatment of cancers, various strategies have been proposed in-the prior art. Thus, Application EP 259 212 describes the preparation of vaccines intended for the treatment of cancers, comprising a modified virus capable of expressing an antigen specific for a tumour, permitting an immune response to be generated against these cells. Moreover, Application WO91/15580 describes the construction of retroviruses containing a gene encoding a ribozyme, whose expression in cell culture can make it possible to destroy an mRNA of an oncogene. It is also known from Application WO93/10814 to use vectors expressing immunogenic, non-tumorigenic forms of cellular oncogenes involved in the development of cancers. Application WO93/02556 finally describes the use of cells removed from the tumour, which are genetically modified ex vivo by the introduction of a toxic gene, then readministered to the patient. However, this approach requires surgical steps, and furthermore, the stability of the toxic gene in the cell transformed ex vivo is not established.

Consequently, although valuable results have been obtained, the constructs described in the prior art do not make it possible to satisfactorily solve some difficulties, and especially the precise screening of the cells to be treated. Thus, it has been proposed to use recombinant retroviruses as vectors for the transfer of therapeutic genes. Indeed, these viruses are capable of infecting only the cells which divide. However, the use of this type of vector does not make it possible to screen, with sufficient selectivity, the tumour cells. Furthermore, these viruses cannot be obtained at very high titres, thereby limiting the therapeutic efficacy. It has moreover been proposed to directly administer the gene into the tumour. Here again, the risks of diffusion to the surrounding cells are not excluded. For this reason, it has been proposed to modify the host specificity of the viruses used, by incorporating into their envelopes proteins recognizing receptors specific for tumour cells (WO93/00130; WO92/14829). However, these constructs do not make it possible to obtain sufficient targeting, especially when the virus used encodes a toxic protein intended for the destruction of the cells.

The present invention provides an advantageous solution to these problems. It provides, indeed, vectors capable of directing the expression of a given gene selectively in the tumour cells. The present invention is based in particular on the demonstration that certain signals for control of transcription are active (or activated) specifically in the tumour cells, and the they can be used for the selective expression of heterologous genes. It also results from the demonstration that adenoviruses constitute particularly effective vectors for the transfer and expression of therapeutic genes in the tumour cells. In particular, adenoviruses have the advantage of not becoming integrated into the genome of the cells which they infect, of being maintained therein in a very stable manner, which makes it possible to obtain a lasting therapeutic effect and to have a very broad host range, which permits application to the treatment of cancers affecting any type of cells. Furthermore, recombinant adenoviruses can be obtained at high titres, which makes it possible to work at high multiplicities of infection, and to introduce several copies of the heterologous gene per cell. The invention is also based on the demonstration that adenovirus-type viruses are capable of incorporating heterologous sequences comprising such promoters, of transferring these sequences into the tumour cells, and of expressing desired genes under the control of specific signals directly in tumours.

A first subject of the invention therefore lies in a defective recombinant adenovirus containing a heterologous DNA sequence under the control of expression signals which are active specifically in tumour cells.

The subject of the invention is also the use of such a defective recombinant adenovirus for the preparation of a pharmaceutical composition intended for the treatment or the prevention of cancers.

The defective adenoviruses according to the invention are adenoviruses which are incapable of autonomously replicating in the target cell. Generally, the genome of the defective adenoviruses used within the framework of the present invention therefore lacks at least sequences necessary for the replication of the said virus in the infected cell. These regions can be either removed (completely or partially), or rendered non-functional, or substituted by other sequences and especially by the inserted gene. Preferably, the defective virus conserves, nevertheless, the sequences of its genome which are necessary for the encapsulation of the viral particles.

There are various serotypes of adenoviruses, whose structure and properties vary somewhat. However, these viruses are not pathogenic for man, and especially for non-immunosuppressed subjects. Among these serotypes, the use of type 2 or 5 human adenoviruses (Ad 2 or Ad 5) or of adenoviruses of animal origin (see Application FR 93 05954) is preferred within the framework of the present invention. Among the adenoviruses of animal origin which can be used within the framework of the present invention, there may be mentioned adenoviruses of canine, bovine, murine (example: MAV1, Beard et al., Virology 75 (1990) 81), ovine, porcine, avian or alternatively simian (example: SAV) origin. Preferably, the adenovirus of animal origin is a canine adenovirus, more preferably a CAV2 adenovirus [Manhattan strain or A26/61 (ATCC VR800) for example].

Preferably, adenovirus of human, canine or mixed origin are used within the framework of the invention.

As indicated above, the adenoviruses of the invention carry a heterologous DNA sequence. This heterologous DNA sequence permits the expression of a desired biological activity in tumour cells. Preferably, the heterologous DNA sequence comprises at least one gene chosen from a gene which is toxic for the infected cell, a gene whose expression makes it possible to at least partially inhibit cell division, or a gene encoding a lymphokine. The adenoviruses of the invention may, in addition, contain several of these sequences, so as to obtain, in some cases, a synergistic anti-tumour effect.

Among the genes which are toxic for the infected cell, there may be mentioned preferably the genes whose expression product confers on the cell sensitivity to a therapeutic agent. More preferably, the toxic gene is chosen from the thymidine kinase gene, whose expression product confers on mammalian cells sensitivity to certain therapeutic agents such as ganciclovir or acyclovir. The thymidine kinase of the herpes simplex virus is capable of phosphorylating nucleoside analogues such as acyclovir or ganciclovir. These modified molecules can be incorporated into a DNA chain undergoing elongation, which has as consequence the stopping of the DNA synthesis, resulting in the death of the cell (F. L. Moolten, Cancer Res. 46 (1986) 5276). This strategy thus makes it possible to remove specifically the cells expressing the suicide gene. Furthermore, the synthesis of DNA being the target of the toxicity, only the cells undergoing division are affected.

More preferably, the thymidine kinase gene of the human herpes virus (hTK HSV-1) is used within the framework of the present invention. The sequence of this gene has been described in the literature (see especially McKnight et al., Nucleic Acid. Res. 8 (1980) 5931).

It is also possible to use the cytosine deaminase gene, whose expression product confers on mammalian cells sensitivity to 5-fluorocytosine (5-FC). Moreover, among the toxic genes which can be used within the framework of the present invention, there may also be mentioned the genes whose expression product induces apoptosis of the infected cell.

Among the genes whose expression makes it possible to at least partially inhibit cell division, there may be mentioned more particularly tumour suppressor genes (or antioncogenes) or any active derivative thereof; antisense sequences or ribozymes, whose expression in the target cell makes it possible to at least partially inhibit the expression of genes promoting cell division.

Among the tumour suppressor genes which can be used within the framework of the present invention, there may be mentioned more particularly the p53 gene (Baker et al., Science 244 (1989) 217); the Rb gene (Friend et al., Nature 323 (1986) 643; Huang et al., Science 242 (1988) 1563); the rap 1A gene (Kitayama et al., Cell 56 (1989) 77); the DCC gene (Fearon et al., Science 247 (1990) 49), the k-rev2 and k-rev3 genes; or any other tumour suppressor genes described in the literature (cf. for example WO91/15580).

The heterologous DNA sequence may also contain an antisense sequence, whose expression in the target cell makes it possible to control the expression of genes promoting cell proliferation. This control may occur during transcription, splicing of the premessenger, degradation of the messenger, its translation into protein, or post-translational modifications. Preferably, the heterologous DNA sequence contains a gene encoding an antisense RNA capable of controlling the translation of a target mRNA (EP 140 308). Among the antisense sequences which can be used within the framework of the invention, there may be mentioned more particularly any antisense sequence which makes it possible to reduce the levels of production of the oncogenes ras, myc, fos, c-erb B, and the like.

Among the genes encoding lymphokines, there may be mentioned more particularly genes encoding interleukins (preferably IL-1 to IL-3), interferons, tumour necrosis factors, colony-stimulating factors (G-CSF, M-CSF, GM-CSF, and the like), TGF-β, and the like. Moreover, the lymphokine-encoding gene generally comprises, upstream of the coding sequence, a signal sequence directing the synthesized polypeptide in the secretion pathways of the target cell. This signal sequence may be the natural signal sequence of the lymphokine, but it may also be any other functional signal sequence, or an artificial signal sequence. Such constructs make it possible in particular to increase the lymphokine levels in a very localized manner, and thus, in the presence of a tumour-specific antigen, to enhance the immune response against a particular type of tumour, which gives a particularly advantageous effect.

As indicated above, the heterologous DNA sequence is placed under the control of expression signals which are active specifically in tumour cells. In this way, the gene used is expressed and produces its effect only when the virus has indeed infected a tumour cell.

In a preferred embodiment of the invention, they are expression signals which are induced by or active in the presence of viruses responsible for or associated with tumours. Still more preferably, an expression signal inducible by the Epstein-Barr virus (EBV) or by the papilloma virus is used within the framework of the present invention.

The Epstein-Barr virus (EBV) is associated with two types of human cancers: Burkitt's lymphoma and cancer of the nasopharynx. The use of a recombinant adenovirus containing a toxic gene under the control of a promoter inducible by EBV makes it possible advantageously to express this toxic gene specially in the tumour cells of the nasopharynx. In biopsies of cancers of the nasopharynx, only one nuclear antigen is regularly present, EBNA1, which is involved in the maintenance of the viral genome in the cells infected by EBV in the latent phase, and which transactivates the viral promoter BCR2. One particular subject of the invention therefore lies in the use, for the specific expression of a gene in nasopharynx cancer cells, of a sequence corresponding to EBNA1 (EBNA1-RE: EBNA1 "responsive element"). In particular, the invention relates to an adenovirus containing, as expression signal, a chimeric promoter containing a sequence corresponding to EBNA1 fused upstream of another viral promoter, the promoter of the terminal protein 1 (TP1) gene. The examples described in the present application indeed show that this chimeric promoter is inducible by EBNA1.

Papilloma viruses (especially the HPV 16 and 18 viruses) are responsible for 90% of cervical cancers in women and have been identified in pre-cancerous epithelial lesions (Riou et al., Lancet 335 (1990) 117). The product of the E6 gene leads to the formation of tumours by substantially decreasing the quantity of wild-type p53, an antioncogene, in HPV-positive cells (Wrede et al., Mol. Carcinog. 4 (1991) 171). The use of a recombinant adenovirus containing a toxic gene under the control of a promoter inducible by HPV (for example protein E6) makes it possible advantageously to express this toxic gene specifically in the corresponding tumour cells.

They may also be expression signals which are inactive in normal cells and active in tumour cells. In particular, it is possible to use within the framework of the present invention the α-foetoprotein promoter (Alpert E., in Hepatocellular carcinoma, Okuda & Peters (eds), New York, 1976, 353) or the P3 promoter of IGF-II (Sussenbach et al., Growth Regulation 2 (1992) 1), which are active in adults, solely in hepatocarcinomas. It is also possible to use promoters induced by hormones in the case of hormone-dependent or hormone-associated tumours (breast or prostate tumours, for example).

In addition, these promoter sequences can be modified by addition of activating or regulatory sequences and the like.

The defective recombinant adenoviruses according to the invention can be prepared by any technique known to persons skilled in the art (Levrero et al., Gene 101 (1991) 195, EP 185 573; Graham, EMBO J. 3 (1984) 2917). In particular, they can be prepared by homologous recombination between an adenovirus and a plasmid carrying, inter alia, the heterologous DNA sequence. The homologous recombination occurs after cotransfection of the said adenoviruses and plasmid into an appropriate cell line. The cell line used should preferably (i) be transformable by the said elements, and (ii) contain the sequences capable of complementing the defective adenovirus genome part, preferably in integrated form in order to avoid risks of recombination. As an example of a cell line, there may be mentioned the human embryonic kidney line 293 (Graham et al., J. Gen. Virol. 36 (1977) 59) which contains especially, integrated in its genome, the left-hand part of the genome of an Ad5 adenovirus (12%). Strategies for constructing vectors derived from adenoviruses have also been described in Applications Nos. FR 93 05954 and FR 93 08596.

Then, the adenoviruses which have multiplied are recovered and purified according to conventional molecular biology techniques, as illustrated in the examples.

The present invention also relates to a pharmaceutical composition containing one or more defective recombinant adenoviruses as described above. Preferably, the pharmaceutical compositions of the invention contain a vehicle which is pharmaceutically acceptable for a formulation directly injectable into the tumours to be treated. This may be in particular isotonic sterile solutions, or dry, especially freeze-dried, compositions which, upon addition, depending on the case, of sterilized water or physiological saline, permit the preparation of injectable solutions. Direct injection into the tumour to be treated is advantageous since it makes it possible to concentrate the therapeutic effect at the level of the affected tissues. However, it is also possible to use pharmaceutical compositions formulated for topical, oral, parenteral, intranasal, intravenous, intramuscular, subcutaneous, intraocular or transdermal administration and the like.

The doses of defective recombinant adenovirus used for the injection can be adjusted according to various parameters, especially according to the mode of administration used, the pathology concerned, the gene to be expressed, or alternatively the duration of treatment desired. Generally, the recombinant adenoviruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectivity of a virus solution, and is determined by infection of an appropriate cell culture, and measurement, generally after 48 hours, of the number of plaques of infected cells. The techniques for determining the pfu titre of a viral solution are well documented in the literature.

The present invention thus offers a very effective means for the treatment of or prevention of cancers. It is most particularly suitable for the treatment of cancers of the nasopharynx or hepatocarcinomas.

In addition, this treatment may apply both to man and any animal such as ovines, bovines, domestic animals (dogs, cats and the like), horses, fish and the like.

The present invention will be more completely described with the aid of the following examples which should be considered as illustrative and non-limiting.

LEGEND TO THE FIGURES

FIG. 1: Representation of the vector pONT-tk

Figure 2:
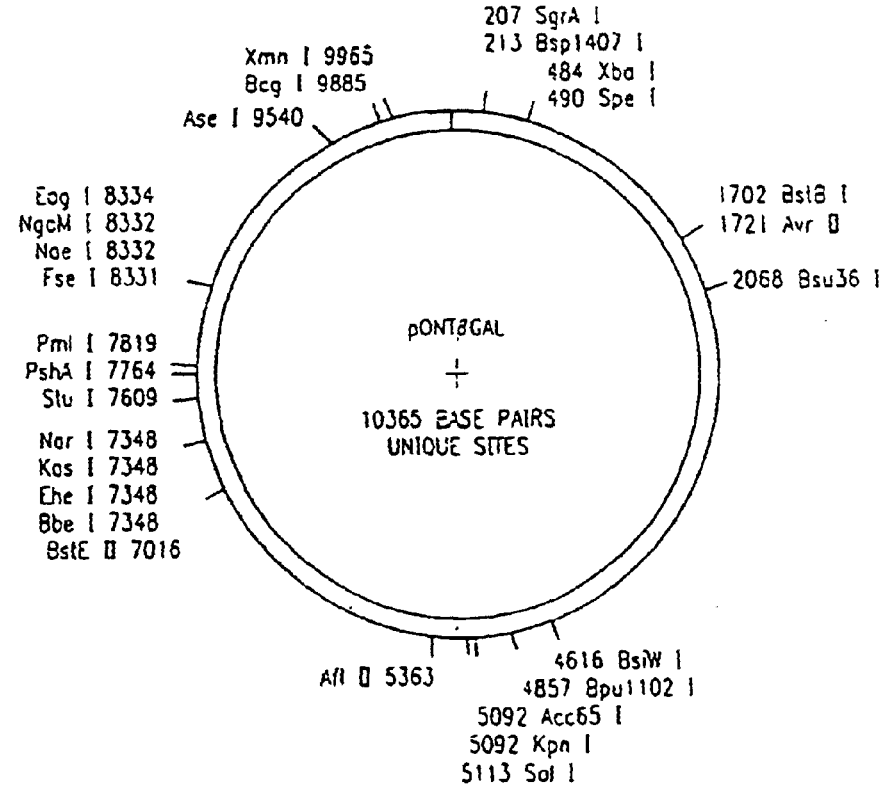

FIG. 2: Representation of the vector pONT-β-gal

GENERAL MOLECULAR BIOLOGY TECHNIQUES

The methods conventionally used in molecular biology, such as preparative extractions of plasmid DNA, centrifugation of plasmid DNA in caesium chloride gradient, agarose or acrylamide gel electrophoresis, purification of DNA fragments by electroelution, phenol or phenol-chloroform extraction of proteins, ethanol or isopropanol precipitation of DNA in saline medium, transformation in Escherichia coli and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The pBR322- and pUC-type plasmids and the phages of the M13 series are of commercial origin (Bethesda Research Laboratories).

For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier.

The filling of the protruding 5' ends can be performed with the Klenow fragment of E. coli DNA polymerase I (Biolabs) according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method developed by Taylor et al. [Nucleic Acids Res. 13 (1985) 8749–8764] using the kit distributed by Amersham.

The enzymatic amplification of the DNA fragments by the so-called PCR technique [Polymerase-catalyzed-Chain Reaction, Saiki R. K. et al., Science 230 (1985) 1350–1354; Mullis K. B. and Faloona F. A., Meth. Enzym. 155 (1987)

335–350] can be performed using a DNA thermal cycler (Perkin Elmer Cetus) according to the specifications of the manufacturer.

The verification of the nucleotide sequences can be performed by the method developed by Sanger et al. [Proc. Natl. Acad. Sci. USA, 74 (1977) 5463–5467] using the kit distributed by Amersham.

EXAMPLES

Example 1.

Construction of the vector Ad-ONT-tk carrying the tk gene under the control of a chimeric promoter EBNA1-RE/TP1 (FIG. 1).

This example describes the construction of a recombinant adenovirus containing the herpes simplex virus thymidine kinase gene (tk) under the control of a promoter which is specifically active in the cells infected by the EBV virus (chimeric promoter EBNA1-RE/TP1).

1.1. Construction of the plasmid p7tk1

This example describes the construction of the plasmid p7tk1 containing the open reading frame of the tk gene of 1131 base pairs (ATG 114-116 and stop codon TGA 1242-1244), which frame is inserted into a multiple cloning site.

The BglII-NcoI fragment containing the herpes simplex virus type 1 thymidine kinase (tk) gene was isolated from the plasmid pHSV-106 (marketed by Gibco BRL), repaired by the action of the klenow fragment and then inserted into the SmaI site of the plasmid pGEM7zf(+) (marketed by Promega). The SmaI and BglII sites are destroyed during this step, the NcoI site is conserved.

The plasmid obtained was designated p7tk1.

1.2. Construction of the plasmid pONT1

This example describes the construction of a plasmid containing a chimeric promoter consisting of a sequence required for the transactivation by the EBNA1 antigen and of the EBV virus TP1 promoter.

The EcoRI(7315)-SmaI(8191) fragment from the EBV virus was isolated from the strain B95-8. The complete sequence of the EBV virus has been described by Baer et al., (Nature 310 (1984) 207). This fragment contains the sequences required for the transactivation by the nuclear 1 antigen (EBNA1) (D. Reisman & B. Sugden, 1986, Molecular and Cellular Biology, vol. 6 pp. 3838–3846). This fragment was then fused to the NruI(166 241)-PstI(166 559) fragment from EBV B95-8 (the PstI site was digested with T4 polymerase), containing the TP1 promoter. The chimeric promoter thus obtained was then inserted into the multiple cloning site of the plasmid pBluescript II SK.

The plasmid obtained was designated pONT1.

1.3. Construction of the plasmid poNTtk

The plasmid pONTtk contains the herpes simplex virus thymidine kinase gene (tk) cloned into the plasmid p7tk1, under the control of the chimeric promoter EBNA1-RE/TP1 cloned into the plasmid pONT1.

To construct this plasmid, the BamHI-XhoI fragment of pONT1 which contains the chimeric promoter transactivated by EBNA-1 and EBNA-2, and the XhoI-ClaI fragment from p7tk1 which contains the tk open reading frame were cloned into the BamHI (478) and ClaI (4550) sites of the plasmid pAd.RSVβgal. The plasmid pAd.RSVβGal contains, in the 5'→3' orientation,

- the PvuII fragment corresponding to the left end of the Ad5 adenovirus containing: the ITR sequence, the replication origin, the signals for encapsulation and the enhancer E1A;
- the gene encoding β-galactosidase under the control of the RSV promoter (Rous sarcoma virus),
- a second fragment from the Ad5 adenovirus genome, which permits homologous recombination between the plasmid pAd.RSVβGal and the adenovirus d1324. The plasmid pAd.RSVβGal has been described by Stratford-Perricaudet et al. (J. Clin. Invest. 90 (1992) 626).

All the cloning sites are conserved. The plasmid obtained was designated pONTtk (FIG. 1).

1.4. Construction of the recombinant adenovirus Ad-ONT-tk

The vector pONTtk was linearized and cotransfected with a deficient adenoviral vector, into helper cells (line 293) providing in trans the functions encoded by the adenovirus E1 regions (E1A and E11B).

More precisely, the adenovirus Ad-ONT-tk was obtained by homologous recombination in vivo between the mutant adenovirus Ad-d1324 (Thimmappaya et al., Cell 31 (1982) 543) and the vector pONTtk, according to the-following procedure: the plasmid pONTtk, linearized with XmnI, and the adenovirus d1324, linearized with the enzyme ClaI, were cotransfected into the line 293 in the presence of calcium phosphate, so as to allow the homologous recombination. The recombinant adenoviruses thus generated were selected by plate purification. After isolation, the DNA from the recombinant adenovirus was amplified in the cell line 293, which leads to a culture supernatant containing the unpurified recombinant defective adenovirus having a titre of-about $10^{10}$ pfu/ml.

The viral particles are generally purified by caesium chloride gradient centrifugation according to known techniques (see especially Graham et al., Virology 52 (1973) 456). The adenovirus Ad-ONT-tk can be preserved at −80° C. in 20% glycerol.

Example 2.

Construction of the vector Ad-ONT-βgal

This example describes the construction of a recombinant adenovirus containing the E. coli beta-galactosidase gene (βgal) under the control of a promoter which is specifically active in the cells infected by the EBV virus (chimeric promoter EBNA1-RE/TP1).

2.1. Construction of the plasmid pONT-βgal

The XbaI-(HindIII) fragment from the plasmid pONT1 which contains the chimeric promoter transactivated by EBNA-1 and EBNA-2 and the fragment (StuI)-KpnI from the plasmid pAd.RSVβgal which contains the β-galactosidase gene were cloned into the XbaI (484) and KpnI (4520) sites of the plasmid pAd.RSVβgal. The HindIII and StuI sites are destroyed during this step. The plasmid obtained was designated pONT-βgal (FIG. 2).

2.2. Construction of the-Ad-OTT-βgal adenovirus

The vector pONT-βgal obtained in Example 2.1, was used, by homologous recombination according to the procedure described in Example 1.4, to prepare a recombinant adenovirus containing the E. coli beta-galactosidase gene (βgal) under the control of the chimeric promoter EBNA1-RE/TP1. The Ad-ONT1-βgal adenovirus thus obtained can be preserved at −80° C. in 20% glycerol.

Example 3.

Construction of the vector pONT-CAT

This example describes the construction of a vector comprising the chloramphenicol acetyltransferase (CAT) gene under the control of a promoter which is specifically active in the cells infected by the EBV virus (chimeric promoter EBNA1-RE/TP1).

3.1. Construction of the vector

The EBV TP1-promoter was isolated in the form of the EBV NruI(166241)-PstI(166559) fragment. This fragment was then fused to the CAT gene, and inserted, in the form of an NruI-BamHI fragment, into the plasmid pGem7ZF (Promega). The resulting plasmid was designated pTP1-CAT. The NruI-BamHI fragment from the plasmid pTP1-CAT was then fused, downstream of the EBV strain B95-8 EcoRI(7315)-SmaI(8191) fragment, containing the sequences required for the transactivation by EBNA1 (cf. Example 1.2.). The fragment obtained, comprising the CAT gene under the control of the chimeric promoter EBNA1-RE/TP1, was inserted into the EcoRI and BamHI sites of the plasmid pBluescript SK in order to generate the plasmid pONT-CAT. A plasmid was also constructed from which the elements for responding to the EBNA2 antigen of the TP1 promoter were deleted. For that, the TP1 promoter was isolated in the form of the EBV NruI(166375)-PstI(166559) fragment. This plasmid was designated pOST-CAT.

3.2. Activity in vitro

This example demonstrates that the constructs described above are induced specifically by antigens of the Epstein-Barr virus.

The vectors pONT-CAT, pOST-CAT and pTP1-CAT were transfected by electroporation into an EBV$^-$ B lymphocyte line (DG75 cells), either alone or in the presence of vectors for expressing the viral antigens EBNA1, EBNA2 or EBNA1+EBNA2. 48 hours after the transfection, the cells were lysed by freezing/thawing, the cell debris removed and then the extracts obtained were standardized depending on the quantity of proteins. The CAT activity was then assayed in these extracts by enzymatic assay. The results obtained are the following:

| | Alone | +EBNA2 | +EBNA1 | +EBNA1:A2 |
|---|---|---|---|---|
| pTP1-CAT | 1 | 35 | 2.5 | 17 |
| pONT-CAT | 1 | 16 | 34 | 136 |
| pOST-CAT | 1 | 1.4 | 19.5 | 22.5 |

These results show clearly that the ONT promoter is specifically active in the presence of the antigens EBNA1 and EBNA2, and that it induces a very high expression of the CAT gene.

We claim:

1. A replication defective recombinant adenovirus comprising a heterologous DNA sequence under the control of an expression signal which is inducible by [the] *an* Epstein-Barr virus (EBV) *antigen*, or by a papilloma virus antigen, *wherein the EBV antigen is EBNA1 or EBNA2, and wherein the papilloma virus antigen is E6.*

2. [An] *The* adenovirus according to claim 1, wherein the expression signal is activated by the EBNA1 antigen, *or the EBNA2 antigen*.

3. [An] *The* adenovirus according to claim 2, wherein the expression signal consists of a chimeric promoter comprising a sequence which is activated by *the* EBNA1 antigen fused upstream of a viral promoter.

4. [An] *The* adenovirus according to claim [1] *2*, lacking regions of its genome which are required for replication in a target cell.

5. [An] *The* adenovirus according to claim 4, wherein said adenovirus is a type Ad5 human adenovirus or a type CAV-2 canine adenovirus.

6. [An] *The* adenovirus according to claim [1] *2*, wherein the heterologous DNA sequence comprises a gene which encodes a product toxic in a cell infected by said adenovirus.

7. [An] *The* adenovirus according to claim 6, wherein said product renders said cell sensitive to a therapeutic agent.

8. [An] *The* adenovirus according to claim 7, wherein the gene is the thymidine kinase gene and the therapeutic agent is ganciclovir or acyclovir.

9. [An] *The* adenovirus according to claim [1] *2*, wherein the heterologous DNA sequence comprises a gene which encodes a product effective to inhibit cell division.

10. [An] *The* adenovirus according to claim 9, wherein the gene is selected from the group consisting of tumour suppressor genes, antisense sequences and ribozymes.

11. [An] *The* adenovirus according to claim 6, wherein the heterologous DNA sequence comprises a gene whose expression product induces apoptosis of a cell infected by said adenovirus.

12. A composition comprising [a] *the* replication defective recombinant adenovirus according to claim [1] *2* and an acceptable carrier.

13. [A] *The* composition according to claim 12, in injectable form.

14. The adenovirus of claim [4] *3*, wherein the viral promoter is the terminal protein 1 (TP1) gene promoter.

15. An isolated cell comprising the adenovirus of claim [1] *2*.

16. The composition of claim 12 comprising from $10^6$ to $10^{10}$ pfu/ml of replication defective recombinant adenoviruses.

*17. The adenovirus according to claim 2, wherein the expression signal is the EBNA1 responsive element (EBNA1-RE).*

*18. The adenovirus according to claim 14, wherein the sequence which is activated by the EBNA1 antigen is the EBNA1 responsive element (EBNA1-RE).*

*19. The adenovirus according to claim 17, wherein said adenovirus is a type Ad5 human adenovirus or a type CAV-2 canine adenovirus.*

*20. The adenovirus of claim 2, wherein the expression signal comprises a promoter sequence from an Epstein-Barr virus.*

*21. The adenovirus according to claim 20, wherein said adenovirus is a type Ad5 human adenovirus or a type CAV-2 canine adenovirus.*

*22. The adenovirus according to claim 20, wherein the promoter sequence is inducible by the EBNA1 antigen.*

*23. The adenovirus according to claim 1, wherein the expression signal is inducible by the papilloma virus E6 antigen.*

*24. The adenovirus according to claim 2, wherein the expression signal comprises a BCR2 viral promoter.*

* * * * *